(12) United States Patent
Reynolds

(10) Patent No.: US 6,841,173 B2
(45) Date of Patent: Jan. 11, 2005

(54) COMPOSITIONS AND METHODS DIRECTED TOWARDS SORE MUSCLES AND JOINTS

(76) Inventor: Peter L. Reynolds, 3401 Old Wagon Rd., Marietta, GA (US) 30062

( * ) Notice: Subject to any disclaimer, the term of this patent is extended or adjusted under 35 U.S.C. 154(b) by 73 days.

(21) Appl. No.: 10/106,607

(22) Filed: Mar. 26, 2002

(65) Prior Publication Data

US 2003/0185904 A1 Oct. 2, 2003

(51) Int. Cl.⁷ ..................... A61K 31/095; A61K 31/10; A61K 31/7008; A61K 31/726; A61K 33/04
(52) U.S. Cl. ........................... 424/702; 514/44; 514/54; 514/55; 514/62; 514/356; 514/423; 514/460; 514/556; 514/561; 514/562; 514/563; 514/706; 514/711; 514/825; 514/906
(58) Field of Search .............................. 514/44, 54, 55, 514/62, 356, 423, 460, 556, 561–563, 706, 711, 825, 906; 424/702

(56) References Cited

U.S. PATENT DOCUMENTS 5,827,886 A * 10/1998 Hersh .......................... 514/562

OTHER PUBLICATIONS

JPAB Abstract JP407255416A, abstracting JP 07/255416 (1995).*
Kavanagh, K. et al., "Oral glycosaminoglycans: a survey of responses," Veterinary Journal, vol. 77(4), 1999, pp. 220–221.*

* cited by examiner

Primary Examiner—John Pak
(74) Attorney, Agent, or Firm—James W. Kayden; Thomas, Kayden, Horstemeyer & Risley, LLP

(57) ABSTRACT

Chemical formulations and methods for reducing muscle and joint soreness are disclosed. A representative chemical formulation includes compounds such as a selenium-compound, chondroitin sulfate, glucosamine, and/or methylsulfonylmethane. A representative method for reducing muscle and joint soreness includes administering the chemical formulation to a host.

11 Claims, No Drawings

COMPOSITIONS AND METHODS DIRECTED TOWARDS SORE MUSCLES AND JOINTS

TECHNICAL FIELD

The present invention is generally related to chemical formulations and methods for administration of the chemical formulation to mammals and, more particularly, is related to chemical formulations directed towards reducing muscle and joint soreness and methods of administration thereof.

BACKGROUND

Often muscle soreness and joint pain occur concurrently as a result of physical exertion or old age. In addition, joint pain may occur as a result of arthritis or other degenerative joint diseases, which may also indirectly cause muscle soreness. Muscle and joint soreness occur in most mammals and, in particular, occur in humans, horses, dogs, and cats. The soreness creates many problems, such as making normal mammalian actions difficult and painful. These actions include walking, squatting, running, grasping, etc. To alleviate this discomfort, multiple pain relievers need to be taken, e.g., one pain reliever to address the muscle soreness and another pain reliever to address joint soreness. Multiple pain relievers, e.g. pills or tablets, can be difficult to administer in same mammals, such as horses, dogs, and cats. Further, there are significant costs associated with purchasing multiple pain relievers.

Selenium compounds, both organic and inorganic, and methylsulfonylmethane have been used for years as mineral supplements to maintain good health and relieve muscle soreness, but not joint pain or soreness. Glucosamine has been shown to be effective for reducing arthritis and soreness of the joints, but not muscle soreness.

Thus, a heretofore unaddressed need exists in the industry to address the aforementioned deficiencies and inadequacies in regard to reducing muscle and joint soreness.

SUMMARY OF THE INVENTION

A representative chemical formulation of the present invention includes compounds such as a selenium-compound, chondroitin sulfate, glucosamine, and/or methylsulfonylmethane. The present invention also involves a method directed towards reducing muscle and joint soreness by administering the chemical formulation to a host.

Other systems, methods, features, and advantages of the present invention will be or will become apparent to one with skill in the art upon examination of the following drawings and detailed description. It is intended that all such additional systems, methods, features, and advantages be included within this description, be within the scope of the present invention, and be protected by the accompanying claims.

DETAILED DESCRIPTION

The present invention provides for chemical formulations and methods of use thereof directed towards reducing muscle and joint soreness. The chemical formulation includes compounds such as a selenium-compound, chondroitin sulfate, glucosamine, and/or methylsulfonylmethane. The methods directed towards reducing muscle and joint soreness include providing an effective amount of the chemical formulation to a host.

One embodiment of the chemical formulation includes combining a selenium-compound with chondroitin sulfate, glucosamine, and/or methylsulfonylmethane. Selenium-compounds and methylsulfonylmethane are effective for decreasing muscle soreness, while chondroitin sulfate and glucosamine are effective for decreasing joint soreness. Another embodiment of the chemical formulation includes combining the selenium-compound, chondroitin sulfate, glucosamine, and methylsulfonylmethane.

The selenium-compounds include, for example, one or more of the following: sodium selenite, sodium selenate, and selenomethionine. In addition, the selenium-compounds include precursor compounds thereof and their pharmaceutically acceptable salts that are useful for reducing muscle soreness.

Chondroitin sulfate includes, for example, any pharmaceutically acceptable salt thereof. In addition, chondroitin sulfate may include precursor compounds (e.g., prodrugs) thereof that are useful in treating sore joints. For example, the precursor compounds may include one or more of the following: mucopolysaccharides, glutamic acid, proline, glycine, and glucuronic acid.

Glucosamine includes, for example, any pharmaceutically acceptable salt thereof. In addition, glucosamine may include precursor compounds thereof that are useful for decreasing joint soreness. For example, the precursor compound may include glutamine.

Methylsulfonylmethane includes, for example, any pharmaceutically acceptable salt thereof. In addition, methylsulfonylmethane may include precursors thereof that are useful for decreasing muscle soreness. An alternate name for methylsulfonylmethane is dimethyl sulfone.

In addition, the chemical formulation includes other compounds that are useful for decreasing joint soreness. For example, the precursor compounds may include one or more of the following: mucopolysaccharides, glutamic acid, proline, glycine, and glucuronic acid.

Some of the compounds used in the chemical formulation of the present invention, such as those containing basic substituents, can form useful salts with various inorganic and organic acids, while compounds containing acidic funtionalities can form useful salts with various inorganic and organic bases. The pharmaceutically acceptable salts of the compounds can be prepared by following procedures that are familiar to those skilled in the art.

The compounds used to produce the chemical formulation described herein may be administered as such, or in the form of a precursor compound from which the compound can be derived. In general, precursor compounds are derivatives of one of the compounds described herein, the pharmacological action of which results from the conversion by chemical or metabolic processes in vivo to the compound.

The chemical formulation of the present invention may be used as the active ingredient in combination with a pharmaceutically acceptable carrier medium. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular administration unit form desired. Except insofar as any conventional carrier medium is incompatible with the compounds used in practicing embodiments of the invention, such as by producing any undesirable biological effect or otherwise interacting in a deleterious manner with any other component(s) of the pharmaceutical composition, its use is contemplated to be within the scope of this invention.

Pharmaceutical organic or inorganic solid or liquid carrier media suitable for enteral or parenteral administration can be used to fabricate the chemical formulation. Gelatin, lactose, starch, magnesium stearate, talc, vegetable and animal fats and oils, gum, polyalkylene glycol, water, or other known carriers may all be suitable as carrier media.

The chemical formulation may be prepared in various forms for administration, including tablets, caplets, pills or dragees, or can be filled in suitable containers, such as capsules, or, in the case of suspensions, filled into bottles, or can be diluted in a liquid such as water. The chemical formulation is preferentially administered via liquid that can be directly or indirectly administered to the host. For example, when the chemical formulation is dissolved in a liquid, the liquid can be directly ingested or the liquid can be mixed with a solid and ingested.

The chemical formulation may be administered orally, rectally, parenterally, such as by intramuscular injection, subcutaneous injection, intravenous infusion or the like, intracisternally, intravaginally, intraperitoneally, locally, such as by powders, ointments, drops or the like, depending on the nature and severity of the muscle and joint soreness. As indicated above, the chemical formulation is preferentially administered orally as a liquid having the chemical formulation dissolved therein.

The chemical formulation described above may be administered using any amount and any route of administration effective for decreasing muscle and joint soreness. Thus, the expression "amount effective to reduce sore muscles and joints", as used herein, refers to a nontoxic but sufficient amount of the chemical formulation to provide the desired reduction in muscle and joint soreness. The exact amount required will vary from host to host, depending on the species, age, size, weight, and general condition of the individual host, the severity of the soreness, the particular chemical formulation and its mode of administration, and the like.

However, the chemical formulation can include about 1 to about 6 milligrams per ounce of a selenium compound, about 500 to about 5000 milligrams of chondroitin sulfate per day, about 1500 to about 6000 milligrams per ounce of glucosamine, and/or about 800 to about 3500 milligrams per ounce of methylsufonylmethane. In another embodiment, the chemical formulation can include about 1.5 to about 3 milligrams per ounce of a selenium compound, about 750 to about 3500 milligrams of chondroitin sulfate per day, about 1750 to about 4000 milligrams per ounce of glucosamine, and/or about 200 to about 2800 milligrams per ounce of methylsufonylmethane. The preferable chemical formulation includes about 2 milligrams per ounce of a selenium compound, about 2000 milligrams of chondroitin sulfate per day, about 3800 milligrams per ounce of glucosamine, and/or about 2400 milligrams per ounce of methylsufonylmethane.

The chemical formulation is preferably formulated in units for ease of administration and uniformity of the amount administered. "Units" as used herein refers to a physically discrete unit of the chemical formulation appropriate for the host. Each unit should contain the quantity of chemical formulation calculated to produce the desired therapeutic affect either as such, or in association with the selected pharmaceutical carrier medium.

By way of example, a suitable amount for oral administration for a large mammal (e.g., a horse) would include a unit of the chemical formulation containing from about 1 to about 6 milligrams of selenium per day, about 500 to about 5000 milligrams of chondroitin sulfate per day, about 1500 to about 6000 milligrams of glucosamine per day, and/or about 800 to about 3500 milligrams of methylsufonylmethane per day. In another embodiment, a suitable amount of the chemical formulation for oral administration for a large mammal would include a unit containing from about 1.5 to about 3 milligrams of selenium per day, about 750 to about 3500 milligrams of chondroitin sulfate per day, about 1750 to about 4000 milligrams of glucosamine per day, and/or about 2000 to about 4800 milligrams of methylsufonylmethane per day. The preferable unit of the chemical formulation for oral administration to a large mammal would include a unit containing about 2 milligrams of selenium per day, about 2000 milligrams of chondroitin sulfate per day, about 3800 milligrams of glucosamine per day, and about 2400 milligrams of methylsufonylmethane per day.

The chemical formulation will typically be administered from 1 to 2 times a day so as to deliver the chemical formulation to conform to the above-mentioned daily unit to be administered. However, the exact regimen for administration of the chemical formulation described herein may be dependent on the needs of the individual host and the judgment of the attending medical specialist. For example, the chemical formulation can be administered in amounts of about 2 milligrams of selenium per day, about 2000 of chondroitin sulfate per day, about 3800 milligrams of glucosamine per day, and/or 2400 milligrams of methylsufonylmethane per day initially, while administering half these amounts for maintenance thereafter.

As used herein, the term "host" includes both humans and animals (e.g., cats, dogs, horses, etc.). In particular, the chemical formulation is suited for decreasing muscle and joint soreness in a large mammal such as a horse.

Embodiment A

TABLE 1

EXEMPLARY CHEMICAL FORMULATION

| Components | Approximate Weight Percent (%) Per Gallon of Liquid |
| --- | --- |
| Water & Other Agents | 87–93 |
| L-Glutamine | 0.3–0.6 |
| L-Proline | 0.2–0.4 |
| L-Glutamic acid | 0.2–0.4 |
| L-Glycine | 0.6–1.1 |
| Glucosamine HCL | 3.9–6.7 |
| Sodium Selenite | 0.01–0.02 |
| Methylsulfonylmethane | 2.4–4.2 |

Table 1 describes an embodiment of the chemical formulation as implemented into a fruit flavored formulation that can be administered to large mammals such as horses. The preferred embodiment of the fruit flavored formulation includes approximately 2 milligrams of the selenium compound per ounce of liquid.

The fruit flavored formulation can be orally administered into the mouth of the horse with a dosing syringe or similar device. In addition, the fruit formulation can be mixed with horse feed. Using either dosing method, approximately 1.0 ounce (e.g., 2 milligrams of selenium) of fruit formulation per 500 pounds of animal weight should be administered. The fruit formulation can be administered one time per day or portions thereof at multiple times per day. For example, if the horse is fed twice a day then approximately 0.5 ounce of fruit formulation is administered at each feeding. Alternatively, approximately 3.0 ounces of fruit formulation can be added to the horse feed per 500 pounds of animal weight for horses having severe muscle/joint soreness.

It should be emphasized that the above-described embodiments of the present invention are merely possible examples of implementations, set forth only for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

What is claimed is:

1. A chemical formulation for reducing joint and muscle soreness comprising:
   a selenium-compound;
   chondroitin sulfate;
   glucosamine; and
   methylsulfonylmethane.

2. The chemical formulation of claim 1, wherein said selenium-compound is selected from the group consisting of sodium selenite, sodium selenate, and selenomethionine.

3. The chemical formulation of claim 1, wherein said glucosamine is a glucosamine salt.

4. The chemical formulation of claim 1, further comprising glutamine.

5. The chemical formulation of claim 1 further comprising glutamic acid, proline, glycine, and glucuronic acid.

6. The chemical formulation of claim 1 further comprising mucopolysaccharides.

7. The chemical formulation of claim 1 having:
   about 1 to about 6 milligrams of the selenium-compound per ounce of chemical formulation;
   about 500 to about 5000 milligrams of chondroitin sulfate per ounce of chemical formulation;
   about 1500 to about 5200 milligrams of glucosamine per ounce of chemical formulation; and
   about 800 to about 3500 milligrams of methylsufonylmethane per ounce of chemical formulation.

8. A method of reducing muscle and joint soreness comprising administering an amount of the chemical formulation of claim 1 effective to reduce the muscle and joint soreness in a host.

9. The method of claim 8, wherein the amount effective to reduce muscle and joint soreness includes about 1 to about 6 milligrams of selenium per day.

10. The method of claim 8, wherein the amount effective to reduce muscle and joint soreness includes about 2 milligrams of selenium per day.

11. The method of claim 8, wherein the route of administration is selected from the group consisting orally, rectally, parenterally, intracisternally, intravaginally, intraperitoneally, and locally.

* * * * *